(12) United States Patent
Garti et al.

(10) Patent No.: US 10,206,965 B2
(45) Date of Patent: Feb. 19, 2019

(54) CAROTENOID FORMULATION

(75) Inventors: Nissim Garti, Ramot (IL); Morris Zelkha, Omer (IL); Tanya Sedlov, Beer Sheva (IL)

(73) Assignee: LYCORED NATURAL PRODUCTS INDUSTRIES LTD., Beer-Sheva (IL)

( * ) Notice: Subject to any disclaimer, the term of this patent is extended or adjusted under 35 U.S.C. 154(b) by 1425 days.

(21) Appl. No.: 12/182,072

(22) Filed: Jul. 29, 2008

(65) Prior Publication Data
US 2008/0287551 A1 Nov. 20, 2008

Related U.S. Application Data

(63) Continuation of application No. 10/496,966, filed as application No. PCT/IL02/00945 on Nov. 26, 2002, now abandoned.

(51) Int. Cl.
| | |
|---|---|
| A61K 36/48 | (2006.01) |
| A61K 36/81 | (2006.01) |
| A23P 10/30 | (2016.01) |
| A23L 5/44 | (2016.01) |
| A23L 33/105 | (2016.01) |

(52) U.S. Cl.
CPC ........... *A61K 36/48* (2013.01); *A23L 5/44* (2016.08); *A23L 33/105* (2016.08); *A23P 10/30* (2016.08); *A61K 36/81* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2,861,891 A | 11/1958 | Bauernfeind et. al. | |
| 4,522,743 A | 6/1985 | Ditter et al. | |
| 4,563,360 A | 1/1986 | Soucie et al. | |
| 5,166,448 A | 11/1992 | Sasaki et al. | |
| 5,208,381 A | 5/1993 | Meyer et al. | |
| 5,460,823 A | 10/1995 | Jensen et al. | |
| 5,543,164 A | 8/1996 | Krochta et al. | |
| 5,552,166 A | 9/1996 | Harada et al. | |
| 5,780,056 A | 7/1998 | Akamatsu et al. | |
| 5,783,176 A | 7/1998 | Meiring et al. | |
| 5,811,609 A | 9/1998 | Jensen et al. | |
| 5,965,183 A * | 10/1999 | Hartal .................. A23L 1/2753 426/250 | |
| 5,968,251 A | 10/1999 | Auweter et al. | |
| 6,235,315 B1 | 5/2001 | Runge et al. | |
| 6,261,598 B1 * | 7/2001 | Runge et al. ............... 424/456 | |
| 6,783,771 B2 * | 8/2004 | Ikekawa et al. ............. 424/461 |
| 2002/0128325 A1 | 9/2002 | Runge et al. | |
| 2003/0064133 A1 * | 4/2003 | Blatt et al. ...................... 426/72 | |

FOREIGN PATENT DOCUMENTS

| | | |
|---|---|---|
| CA | 2194796 | 1/1996 |
| DE | 44 24 085 A | 1/1996 |
| DE | 19541958 | 5/1997 |
| EP | 0228485 | 7/1987 |
| EP | 0 382 067 A1 | 8/1990 |
| EP | 0 832 569 A2 | 4/1998 |
| EP | 0986963 | 3/2000 |
| GB | 1363623 A | 8/1974 |
| GB | 1561663 A | 2/1980 |
| WO | WO 91/06292 A | 5/1991 |
| WO | WO 94/19411 | 10/1994 |
| WO | 9726803 | 7/1997 |
| WO | WO 97/26802 A | 7/1997 |
| WO | WO 97/48287 | 12/1997 |
| WO | WO 98/16204 | 4/1998 |
| WO | WO 02/41711 A | 5/2002 |

OTHER PUBLICATIONS 2010, http://www.greatvistachemicals.com/vitamins-vitamin/ascorbic-acid.html.*
Hettiarachchy et al., 1988, ACS Symposium Series; American Chemical Society, Washington DC, Ch. 6, Functional Properties of Soy Proteins.*
Frederick J Francis, editor.Gelatin. Encyclopedia of Food Science and Technology, 2nd edition. 4 Vols. New York: John Wiley & Sons, 2000. 1183-1188.*
Schneider, et al., Physik fur Ingenieure, 1991. pp. 288-291.
Fennema, Owen R., Food Chemistry (Third Edition), 1996, pp. coverpages, and 905-906.
Francis, Gelatin. Encyclopedia of Food Science and Technology, 2nd edition, 2000, pp. 1-11.
Gennadios, A., Proteins as Raw Materials for Films and Coatings: Definitions, Current Status, and Opportunities, Protein-Based Films and Coatings, Jul. 2, 2002. pp. 1-41, chapter 1.
Perez-Gago, et al., Water Vapor Permeability, Solubility, and Tensile Properties of Heat-denatured versus Native Whey Protein Films. Journal of Food Science, 1999, pp. 1034-1034, vol. 64, No. 6.
Si-Nang, et al., Determination of Coating Thickness of Microcapsules and Influence upon Diffusion. Journal of Pharmaceutical Sciences, Mar. 1973. pp. 452-455, vol. 62, No. 3.
Ascorbyl palmitate, Wikipedia, https://en.wikipedia.org/wiki/Ascorbyl_palmitate, Oct. 15, 2015, pp. 1-2: Plamitinsäureascorbylester, https://de.wikipedia.org/wiki/Plamitinsäureascorbylester, Oct. 19, 2015, pp. 1-2.
Lycopene, Wikopedia, https://en.wikipedia.org/wiki/Lycopene, Oct. 19, 2015, pp. 1-9: Lycopin, https:/de.wikipedia.org/wiki/Lycopin, Aug. 11, 2015, pp. 1-5.
Molkenprotein, Wikipedia, https://de.wikipedia.org/wiki/Molkenprotein. Oct. 15, 2015, pp. 1-3 with English machine translation.

(Continued)

*Primary Examiner* — Terry A McKelvey
*Assistant Examiner* — Catheryne Chen
(74) *Attorney, Agent, or Firm* — Browdy and Neimark, P.L.L.C.

(57) ABSTRACT

The present invention discloses the use of a lycopene coated with a water non-soluble thin film comprising amphiphilic protein polymer for coloring with red color, foods, pharmaceuticals or cosmetics having fat and/or oil contents higher than 5%. The invention further discloses a process for the preparation of stable lycopene formulation comprising (a) treating an isolated protein to form a protein in a molecular form; (b) dispersing lycopene in an aqueous solution comprising an isolated protein in a molecular form; (c) grinding said dispersion to form lycopene particle size of 1 to 10 μm forming an homogenized mixture comprising fine particles; and optionally (d) drying the homogenized mixture.

17 Claims, No Drawings

(56) References Cited

OTHER PUBLICATIONS

Transparency, Wikipedia, https://en.wikipedia.org/wiki/Transparency, Oct. 15, 2015, pp. 1-3: Transparenz (Physik), https://de.wikipedia.org/wiki/Transparenz_(Physik), Jul. 14, 2015, pp. 1-4.
Hippel, P.H. and Harrington, W.F., "Enzymic studies of the gelatin->Collagen-fold transition"; Biochimca et Biophysica Acta 36: 427-447 (1959).

* cited by examiner

CAROTENOID FORMULATION

FIELD OF THE INVENTION

The present invention is in the field of lycopene formulations, a process for their preparation and their use as additives and in particular as colorants retaining lycopene's unique color.

BACKGROUND OF THE INVENTION

Lycopene, belonging to the carotenoid family of natural substances is abundant in various fruits and vegetables. The compound as found in nature has a trans/cis ratio of 90:10, is insoluble in water and has a rather limited solubility in oil or fat. Studies have shown that frequent consumption of lycopene is associated with decrease of chronic disorders such as cardiac and circulatory disorders. In addition, it may contribute to prevention of several types of cancers. Its protective function is attributed to the fact that lycopene acts as an effective antioxidant. Its unique intense red color led to its use as a natural food colorant. Lycopene may be obtained, either synthetically (EP 382,067) or extracted from tomatoes (WO 97/48,287) which have a relatively high concentration of lycopene.

However, use of lycopene as a food supplement is associated with several problems. Its solubility profile is problematic, being insoluble in water and only sparingly soluble in oils and fats. In addition, it is easily oxidized. In addition, lycopene exhibits its unique red color only as long as it is dispersed in water and the particles have a size of 1-10 μm, preferably 1-3 μm. Particles of higher dimensions are less effective colorants. Furthermore, upon contact with oil the lycopene particles dissolve imparting an orange to yellow color.

As a result, lycopene is used only in dedicated formulations, where the lycopene is protected from oxidation by certain additives and/or the lycopene is present as finely divided particles. WO 91/06292 and WO 94/19411 describe the grinding of β-carotene achieving a particle size of ca. 2-10 μm. Dry powders containing lycopene for use as water dispersible powders were reported in EP 832569 and WO 98/16204. Stable pulverulent lycopene formulations comprising lycopene having a degree of crystallinity of greater than 20% are disclosed in U.S. Pat. No. 6,235,315. The stability of the pulverulent formulation is augmented by addition of protective colloids, stabilizers and plasticizers. US 2002/0128325 discloses a process for producing powders of stabilized carotenoids, where a carotenoid is dispersed in a solution containing a protective colloid and lactose, and the use of such powders in pharmaceuticals, food and cosmetics.

SUMMARY OF THE INVENTION

The present invention is based on coating solid crystallized micronized lycopene particles with a thin film comprising of water soluble amphiphilic biopolymers such as proteins or a mixture of proteins and hydrocolloids to form, once precipitated on the lycopene, a film of water non-soluble net work. Such film formation yields protected lycopene that once placed in an aqueous phase containing lipids, prevents the lycopene from migration in its solid form or molecular form into the lipids/oil/fats. Such coated lycopene thus makes it possible to use lycopene in lipid phases maintaining its typical red color, where migration into the lipid/oil/fat phase would result in a molecular yellow hue. Such a coated lycopene may thus be used as an additive or colorant in foods, pharmaceuticals or cosmetic preparations having lipid contents higher than 5%.

Thus the present invention is directed to the use of a lycopene coated with a water non-soluble thin film comprising amphiphilic protein polymer for coloring with red color, foods, pharmaceuticals or cosmetics having fat and/or oil contents higher than 5%. The water non-soluble film may further comprise a colloid. The coated lycopene can be of any source of lycopene, e.g., synthetic lycopene, tomato pulp, or lycopene extracted from biomass, preferably from tomato pulp.

The present invention is further directed to a process for the preparation of stable lycopene formulation comprising:
 (a) treating an isolated protein to form a protein in a molecular form;
 (b) dispersing lycopene in an aqueous solution comprising an isolated protein in a molecular form;
 (c) grinding said dispersion to form lycopene particle size of 1 to 10 μm forming an homogenized mixture comprising fine particles; and optionally
 (d) drying the homogenized mixture.

The process may further comprise the step of mixing said lycopene particles with at least one colloid in water followed by drying. Optionally, the lycopene may be grinded separately and then added to the aqueous solution of isolated protein.

The lycopene used may be of any source, e.g., synthetic, naturally extracted or a crude biomass-comprising lycopene. The formulation may further comprise antioxidants and/or emulsifiers. All additives to the lycopene forming the formulation are food-grade.

The present invention is further directed to a lycopene containing dry powder obtained by the above process. Such a dry powder is having typically a lycopene content of 1% to 15% (w/w), preferably from 4% to 8%.

The present invention is yet further directed to a method for coloring in red natural color, foods, cosmetics or pharmaceuticals having an oil or fat contents of at least 5% using the dried homogenized lycopene formulation.

DETAILED DESCRIPTION OF THE INVENTION

The following description is illustrative of embodiments of the invention. The following description is not to be construed as limiting, it being understood that the skilled person may carry out many obvious variations to the process.

Throughout the description, percentages are weight by weight unless specifically noted differently. The term "lipid" encompasses oil and fat.

As mentioned the present invention is directed to the use of lycopene coated with a water non-soluble thin film comprising amphiphilic protein polymer for coloring with red color, foods, pharmaceuticals or cosmetics having lipid contents higher than 5%. The invention is further directed to a process for formulating lycopene enabling its use in foods, pharmaceutical or cosmetic preparations having a lipid content higher than 5% maintaining its red color. Lycopene upon coming into contact with foods pharmaceutical or cosmetic preparations having such oil or fat contents tends to dissolve in the lipid phase. The result of such dissolving is the loss of its unique red color. Thus in order to prevent such migration and enable the use of lycopene as an additive to such matrices having high oil or fat contents maintaining its unique red color, a process for the coating of lycopene is disclosed. According to the present invention the lycopene is coated with a transparent film thus prohibiting the migration of the lycopene into the oil or fat phases. The transparent film is composed of an amphiphilic protein. Another option is to add a colloid to the protein-coated lycopene. The lycopene crystal that may be coated according to the present invention may be in any of its forms, non-limiting examples being synthetic lycopene, lycopene extracted from its natural source, e.g. tomatoes or even a crude biomass-comprising lycopene. The amphiphilic proteins used by the present invention are proteins which posses lipophilic amino acids in their chains. Examples of amino acids that impart the desired lipophilicity are leucine, isoleucine, phenylalanine and valine. In addition, proteins that consist of low contents of cystine and cystein in their chains and that tend to cross-link only under extreme conditions of pressure or temperature can be used. Such proteins are surface active and upon an interaction with lycopene, in any of its forms, interact with lycopene fibers or particles and adsorb thereon, forming a thin layer of protein coating on the lycopene fiber or particle. Non limiting examples of proteins are hydrophobically modified soy proteins, whey protein isolates, egg albumin, lysozymes, modified pea proteins and gelatin or mixtures thereof. Modification of proteins may be done either by hydrolizing the proteins, by chemical reaction or by enzymes. The protein in its natural 3-dimensional structure can not be used as a coating film. Rather, the protein should initially be transferred into molecular form by dispersing the protein in water, adjusting the pH to the range of 9 to 10, heat the dispersion, cool and lyophilize.

Certain colloids may be attracted to proteins by hydrophobic or by charge interactions to form protein-colloid complexes. Thus in addition to coating of lycopene by amphiphilic protein, the lycopene according to the present invention may be coated by a protein-colloid film resulting from the interaction of the amphiphilic protein with colloids, forming a coating film comprising of protein and colloid. Such a film, if strongly and effectively adsorbed, is resistant to water dilution and protects lycopene from migrating into oil or fat phases. Non limiting examples of colloids are proteinceous polysaccharides hydrocolloid or protective colloids, wherein said proteinceous polysaccharides hydrocolloid is selected from the group consisting of gum arabic, xanthan gum, amidated starch, amidated pectins; and said protective colloids are selected from the group consisting of food grade polysaccharides, polysaccharides, or gums selected from pectins, alginates, xanthan, tragacanth, or their modified structures, modified starch, modified chitosans, maltodextrin, modified methylcellulose, galactomannan or mixtures thereof.

The lycopene powder, either as a dry biomass, crystalline lycopene or wet biomass, is formulated according to the present invention by dispersing lycopene in an aqueous solution comprising an isolated protein in molecular form and the dispersion is grind homogenized to give lycopene particles having a particle size of from 1 to 10 μm, preferably from 1 to 5 μm and most preferably from 1 to 3 μm. It should be understood that the grinding is a prerequisite enabling the coating of the lycopene by the protein. Such grinding ensures the coating of the entire lycopene fiber or particle in a protein film. The resulting solution comprising of the coated lycopene may be used for coloring and/or additive in foods, pharmaceuticals or cosmetics. Alternatively, the lycopene may be dried to yield a powder, which has a lycopene content of from 1% to 15% (w/w), preferably from 2% to 10% and most preferably from 4% to 8%.

As mentioned the protein film coating the lycopene may further interact with colloids utilizing possible hydrophobic or charge interactions thus forming a coating film comprising of colloid bound protein. It should be noted that the coating film, either protein or protein/colloid may further comprise antioxidants and/or emulsifiers added at the stage of grinding. Such antioxidants and/or emulsifiers are added at the stage of added at least one colloid. Non limiting examples of antioxidants are ascorbic acid, citric acid, tocopherol or ascorbel palmitate. A mixture of ascorbic and citric acids (1:1 wt. ratio) is added to the mixture comprising of the lycopene/protein dry powder and colloid in water. Non limiting examples of emulsifiers are Tween, polyglycerols esters, sugar esters, lecitins, castor oil and ethoxylated castor oil.

According to a specific embodiment of the present invention, the coated lycopene is used as a colorant for foods, pharmaceuticals and cosmetics. Accordingly, the coated lycopene formulation is added to foods, pharmaceuticals and cosmetics to impart a red color. Said lycopene formulation is added to the foods, pharmaceuticals and cosmetics during the process of their preparation. The stage at which the lycopene formulation is added in said preparation process may vary and may be determined by the skilled artisan.

The amount of lycopene formulation effective for imparting the desirable red color to the product may vary. The amount of lycopene formulation added is calculated on the basis of lycopene, wherein the amount of lycopene is 10 to 200 ppm.

The invention will now be described by the following non-limiting examples, where it should be stressed that calculation of tomato pulp to soy mass weight ratios is based on 10-200 ppm Lycopene in said final composition. The tomato pulp is a biomass of tomato after the removal of most of the water-soluble fraction. The tomato pulp may be used as is or dried prior to its use.

EXAMPLES

Example 1

Process for Coating Crystalline Lycopene 100 g isolated Soy protein SUPRO® EX34K (Protein Technologies International Belgium) were dissolved in 1000 g water (30 minutes at 40-50° C.). 50 g pure crystalline lycopene (Lyc-O-Mato® 70%) were added to the solution. Thorough mixing resulted in a homogenous mixture, which was grounded in a ball-mill to yield lycopene having a particle size of 1-3 μm. The ground lycopene was mixed with 650 g modified starch (Mira cup, Staley, USA) and 1000 g water (TDS of mixture ca. 30%). The mixture was immediately spray dried to a cold water dispersible oil resistant powder having a lycopene contents of ca. 6% (Lyc-O-Mato® 6% OR).

Example 2

Industrialized Process for Coating Crystalline Lycopene 2.5 kg of Soy Isolated Protein EX 33K (PTI Production) were dissolved to yield a 6% protein water solution (41.7 kg solution) pH adjusted in the range of 9-10 and the solution was cooked for 1 hr at 80° C. The antioxidants, Ascorbyl Palmitate and α-Tocopherol were added at an amount of 1% (0.04 kg each) from total solids (pH maintained in the range of 9-10). 1 kgP of lycopene (1.54 kg 65% lycopene) were homogenized with the protein solution {where the resulting 43 kg solution may be used as a mixture for drinking comprising of 4.12 kg total solids and 2.32% lycopene}. The homogenized protein-lycopene solution is ground after which are add 7.7 kg of Mira cap (modified starch) and homogenized. TDS before drying 23.3% Lycopene concentration in dry finish product 8.04% with 5% moisture. The quantities of each component are summarized in the table below.

| | |
|---|---|
| Lyc-O-Mato 70% | 1 kgPure (1.54 kg as is) |
| Protein EX 33K | 2.5 kg |
| Ascorbyl Palmitate | 0.04 kg |
| α-Tocopherol | 0.04 kg |
| Mira cap | 7.7 kg |
| Total solids | 11.82 kg |
| Lycopene in dry product | 8.46% |
| Lycopene in dry powder with 5% moisture | 8.04% |

Application: 1000 g of vegetable protein mass (fat contents of 16%) mixture with 0.8 g of Lyc-o-mato® 8% OR. Pack in polyethylen casing and cooking 30 min at 90° C. Colour after cooking—pink, without orange hue.

Example 3

Disperse 0.1g isolated soy protein EX-34 K in 99 g $H_2O$. Adjust pH of suspension to 9.2 with 0.5 M NaOH. Heat the dispersion at 70° C. for 30min. Cool to room temperature and dry by lyophilization. Dissolve 0.1g of lyophilized powder (water-soluble protein) in 100 g $H_2O$. Add 10 g of tomato pulp Lycored). Homogenize pulp suspension using "Silverson" dispersing machine (1000 rpm). Dry pulp with protein by spray dry method.

Application: Add dried powder (10.1 g) to 1270 g soy mass ("Tivall"), homogenize, pack under vacuum in special cover, heat in water (90° C., 15 min.) and store. The soy mass remains with a pink-red color.

Example 4

Disperse 0.1 g isolated soy protein EX-34 K in 99 g $H_2O$. Adjust pH of suspension to 9.2 with 0.5 M NaOH. Heat the dispersion at 70° C. for 30 min. and cool to room temperature. Add 10 g of tomato pulp (Lycored) to prepared solution (of water-soluble protein). Continue further like in Example 3.

Example 5

Disperse 0.05 g isolated soy protein EX-34K in 99 g $H_2O$. Adjust pH of suspension to 10.2 with 0.5 M NaOH. Heat the dispersion at 70° C. for 30 min and cool to room temperature. Dry by lyophilization. Dissolve 0.1 g of lyophilized powder in 100 g $H_2O$. Add 10 g of tomato pulp (LYCORED colorant). Homogenize suspension. Dry by spray dry method.

Application: Add dried powder to 1270 g soy mass ("TIVALL soy protein"), homogenize, pack under vacuum in special cover, heat in water (90° C., 15 min.) and store. The soy mass remains with a pink-red color.

Example 6

Disperse 0.2 g of isolated soy protein 590 in 99 g $H_2O$. Adjust pH of suspension up to 9.2 as per need with 0.5 M NaOH. Heat the dispersion at 70° C. for 30 min. Cool to room temperature and dry by lyophilization. Dissolve 0.2 g of lyophilized powder in 100 g $H_2O$. Add 11 g of tomato pulp (LYCORED colorant), homogenize pulp suspension (Silverson machine). Dry pulp with protein by spray dry method. Application: Add dry powder (11.2 g) to 1270 soy mass ("TIVALL soy protein"), homogenize, pack under vacuum in specific cover, heat in water (90° C., 15 min.) and store. The soy mass remains with a pink-red color.

Example 7

Disperse 0.5 g isolated soy protein 590 in 99 g $H_2O$. Adjust pH of suspension to 9.4 with 0.5 M NaOH. Heat the dispersion at 70° C. for 30 min. Cool to room temperature. Add 10 g of tomato pulp (LYCORED colorant) to prepared solution of water-soluble protein. Homogenize dispersion (Silverson machine) and dry by spray dry method.

Application: Add dry powder (10.5 g) to 1270 g soy mass ("TIVALL soy protein"), homogenize, pack under vacuum in special cover, heat in water (90° C., 15 min.) and store.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

The invention claimed is:

1. A method for coloring with a red coloring material a food, pharmaceutical or cosmetic composition having a fat and/or oil content greater than 5% comprising lycopene coated with a water non-soluble thin film comprising an amphiphilic protein polymer, comprising dispersing lycopene crystals in an aqueous solution comprising an amphiphilic protein polymer, grinding said lycopene crystals to a particle size of 1 to 10 µm in said solution, thereby coating said lycopene crystals with a film comprising said amphiphilic protein polymer, to obtain coated, ground lycopene crystals, preparing a particulate red coloring material comprising said coated, ground lycopene crystals, and incorporating the red coloring material in a red coloring-effective amount in the food, pharmaceutical or cosmetic composition containing greater than 5% of a fat and/or oil, wherein the coated ground lycopene crystals are constructed and adapted to be protected and are protected from dissolution in the fat and/or oil in the food, pharmaceutical or cosmetic, whereby the lycopene crystals retain their red coloring.

2. The method according to claim 1, wherein said lycopene is selected from the group consisting of synthetic lycopene, lycopene extracted from tomato pulp, and lycopene extracted from biomass.

3. The method according to claim 1, wherein said amphiphilic protein is selected from the group consisting of hydrophobically modified soy proteins, whey protein isolates, egg albumin, lysozymes, modified pea proteins, gelatin or mixtures thereof.

4. The method according to claim 1, wherein said water non-soluble thin film further comprises a colloid.

5. The method according to claim 4, wherein said colloid is selected from the group consisting of gum arabic, xanthan gum, amidated starch, amidated pectins, food grade polysaccharides, pectins, alginates, xanthan, tragacanth, modified pectins, modified alginates, modified xanthan, modified tragacanth, modified starch, moditified chitosans, maltodextrin, modified methylcellulose, galactomannan and mixtures thereof.

6. The method of claim 1, wherein the red coloring material of crystalline lycopene coated with a water non-soluble thin film comprising an amphiphilic protein polymer is a product obtained by
 a. treating an isolated protein to form a protein in a molecular form;
 b. dispersing lycopene in an aqueous solution comprising an isolated protein in a molecular form;
 c. grinding said dispersion to form lycopene particle size of 1 to 10 μm forming an homogenized mixture comprising fine particles; and optionally
 d. drying the homogenized mixture; and/or optionally
 e. mixing said lycopene particles obtained in (c) or dry powder obtained in (d) with at least one colloid in water followed by drying.

7. The method of claim 2, wherein the lycopene is extracted from tomato pulp.

8. The method of claim 1, wherein said red coloring material is in dry powder form.

9. The method of claim 1, wherein said red coloring material comprising crystalline lycopene further comprises an anti-oxidant and/or an emulsifier.

10. The method of claim 9, wherein said antioxidant is present and is ascorbic acid, citric acid, tocopherol or a mixture of two or more thereof.

11. The method of claim 1, wherein the ground crystalline lycopene is present in said coloring material in an amount of 1 to 15% (w/w).

12. The method of claim 1, wherein the ground crystalline lycopene has a particle size of 1 to 3 μm and comprises 4 to 8% (w/w) of the coloring material.

13. The method of claim 1, wherein the red coloring material comprising coated, ground lycopene crystals is a material obtained by dispersing crystalline lycopene in an aqueous solution comprising an isolated protein in molecular form, grinding the aqueous solution to homogenize the lycopene to provide lycopene particles having a particle size of 1 to 10 μm, and providing a protein coating on the lycopene particles in the form of a thin protein film, drying to provide a powder, and coating the protein-coated crystalline lycopene powder with a colloid.

14. A method for coloring a food, pharmaceutical or cosmetic with a red coloring material, comprising
 incorporating a red coloring-effective amount of the red coloring material in the food, pharmaceutical or cosmetic, wherein
  said red coloring material is in particulate form and comprises crystalline lycopene particles of 1-10 μm each coated with a film comprising an amphiphilic protein polymer,
  the lycopene comprising 1-15% (w/w) of the particulate coloring material, and
  the food, pharmaceutical or cosmetic has a fat and/or oil content greater than 5%.

15. The method of claim 14, wherein the red coloring material is a product obtained by
 a. treating an isolated protein to form a protein in a molecular form;
 b. dispersing lycopene in an aqueous solution comprising an isolated protein in a molecular form;
 c. grinding said dispersion to form lycopene particle size of 1 to 10 μm forming an homogenized mixture comprising fine particles; and optionally
 d. drying the homogenized mixture.

16. The method of claim 14, wherein said red coloring material is in dry powder form.

17. The method of claim 1 wherein the amount of lycopene incorporated into said composition being in the range of 10-200 ppm.

* * * * *